US007807469B2

(12) United States Patent
Orth et al.

(10) Patent No.: US 7,807,469 B2
(45) Date of Patent: Oct. 5, 2010

(54) METHODS FOR DETERMINING THE FEEDING HABITS OF AN ANIMAL

(75) Inventors: Robert G. Orth, Gerald, MO (US); Graham P. Head, St. Louis, MO (US); Mary Mierkowski, Bridgeton, MO (US); Steven H. Modiano, Manchester, MO (US); John T. Greenplate, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1006 days.

(21) Appl. No.: 11/592,044

(22) Filed: Nov. 1, 2006

(65) Prior Publication Data
US 2007/0099303 A1    May 3, 2007

Related U.S. Application Data

(60) Provisional application No. 60/732,593, filed on Nov. 2, 2005.

(51) Int. Cl.
  *G01N 33/92* (2006.01)
(52) U.S. Cl. .............................. 436/71; 436/63; 436/86; 436/94; 436/174; 436/178
(58) Field of Classification Search .................... 436/63, 436/71, 86, 94, 174, 177, 178
  See application file for complete search history.

(56) References Cited

U.S. PATENT DOCUMENTS

| | | | |
|---|---|---|---|
| 6,537,744 B1 | 3/2003 | Al-Bayati | |
| 6,551,962 B1* | 4/2003 | Pershing et al. | 504/100 |
| 6,868,634 B2 | 3/2005 | Parker | |
| 6,880,771 B2 | 4/2005 | Deppermann | |
| 2003/0186813 A1 | 10/2003 | Pershing et al. | |
| 2007/0011773 A1* | 1/2007 | Clough et al. | 800/279 |
| 2008/0226753 A1* | 9/2008 | Cosgrove | 424/725 |

FOREIGN PATENT DOCUMENTS

WO  WO 2004/086868  10/2004

OTHER PUBLICATIONS

Bontemps et al., Managing the evolution of *Bacillus thuringiensis* resistance in natural populations of the European corn borer, *Ostrinia nubilalis*: host plant, host race and pherotype or adult males at aggregation sites, Proc. R. Soc. Lond. (2004) 271, 2179-2185.
Ferre et al., Biochemistry and genetics of insect resistance to *Bacillus thuringiensis*, Annu. Rev. Entomol., (2002) 47:501-33.
Fred Gould and Michael B. Cohen, Sustainable Use of Genetically Modified Crops in Developing Countries, Agricultural Biotechnology and the Poor, (2000) pp. 139-146.
Gould et al., *Bacillus thuringiensis*—toxin resistance management: Stable isotope assessment of alternate host use by *Helicoverpa zea*, PNAS (2002) 99;16581-16586.
Gould et al., Scientists Find New Way to Assess Where Cotton-Killing Pests Develop, http://www.ncsu.edu/news/press_releases/02_12/317.htm, (Dec. 3, 2002) pp. 1-3.
Kleter et al., New developments in crop plant biotechnology and their possible implications for food product safety (Literature study under commission of the foundation "Consument en Biotechnologie", http://www.rikilt.wageningen-ur.nl/Publications/Publications/tekstrapport2000%20004.htm, (Mar. 2000), pp. 1-51.
Moellenbeck et al., Insecticidal proteins from *Bacillus thuringiensis* protect corn from corn rootworms, Nature Biotechnology, (2001) 19, 668-672.
Ken Ostlie, Crafting crop resistance to corn rootworms, Nature Biotechnology, (2001) 19, 624-625.
Rojas et al., Metabolism of Gossypol by *Heliothis virescens* (F.) (Lepidoptera: Noctuidae), Environ. Entomol., (1992) 21, 518-526.
Dustin R. Rubenstein and Keith A. Hobson, From birds to butterflies: animal movement patterns and stable isotopes, Trends in Ecology and Evolution, (2004), 19(5) 256-263.
R. David Simpson, Managing Genetically Modified Crops for Pest Resistance and Biodiversity, http://www.rff.org/projectdetailpage.cfm?projectID=178.
Philip L. Staddon, Carbon isotopes in functional soil ecology, Trends in Ecology and Evolution, (2004), 19(3) 148-154.
Xi Wang and Leslie C. Plhak, Monoclonal Antibodies for the Analysis of Gossypol in Cottonseed Products, J. Agric. Food Chem., (2004), 52, 709-712.
Xi Wang and Leslie C. Plhak, Production, Characterization, and Application of Anti-Gossypol Polyclonal Antibodies, J. Agric. Food Chem., (2000), 48, 5109-5116.
Liliane Ruess et al., Nitrogen isotope ratios and fatty acid composition as indicators of animal diets in belowground systems, Oecologia, (2004) 139:336-346.
Mehmet Bashan, Effects of Various Diets on the Total Lipid Compositions of the Black Cricket *Melanoglyllus desertus* Pall.*, Tr. J. of Zoology 20, (1996) 375-379.
J.W. Barnett et al., Growth and Fatty Acid Composition of Bollworms, *Heliothis zea* (Lepidoptera: Noctuidae), as Affected by Dietary Fats, Annals of the Entomological Society of America, vol. 63, No. 4, (1970) 917-924.
Hiroyuki Shimasaki et al., Direct transesterification of lipids in mammalian tissue for fatty acid analysis via dehydration with 2,2'-dimethoxypropane, Journal of Lipid Research, vol. 18 (1977) 540-543.
Karla S. Ritter, Metabolism of $\Delta^0$ -, $\Delta^5$ -, and $\Delta^7$ -Sterols by Larvae of *Heliothis zea*, Archives of Insect Biochemistry and Physiology, (1984) 1:281-296.

* cited by examiner

*Primary Examiner*—Maureen M Wallenhorst
(74) *Attorney, Agent, or Firm*—James E. Davis; Joseph A. Schaper; Harness, Dickey & Pierce, P.L.C.

(57) ABSTRACT

A method of determining whether an animal has ingested a plant of interest is provided. The method includes screening the animal for the presence of at least one indicator of a plant of interest.

24 Claims, 4 Drawing Sheets

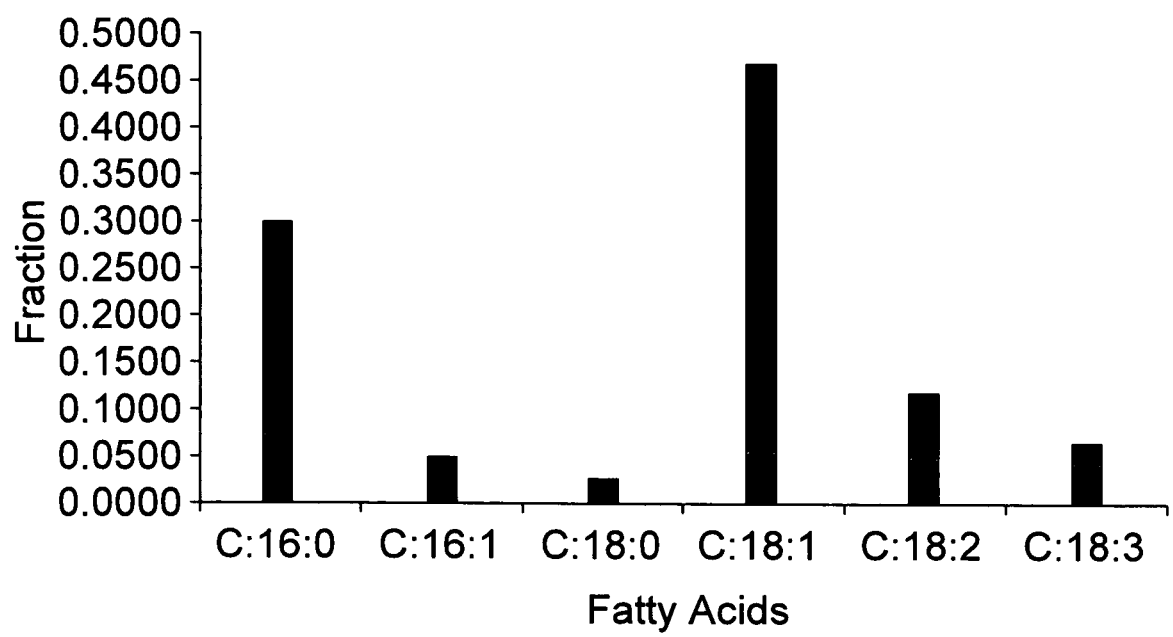
Fig. 1: Fatty Acid profile Cotton raised Moth

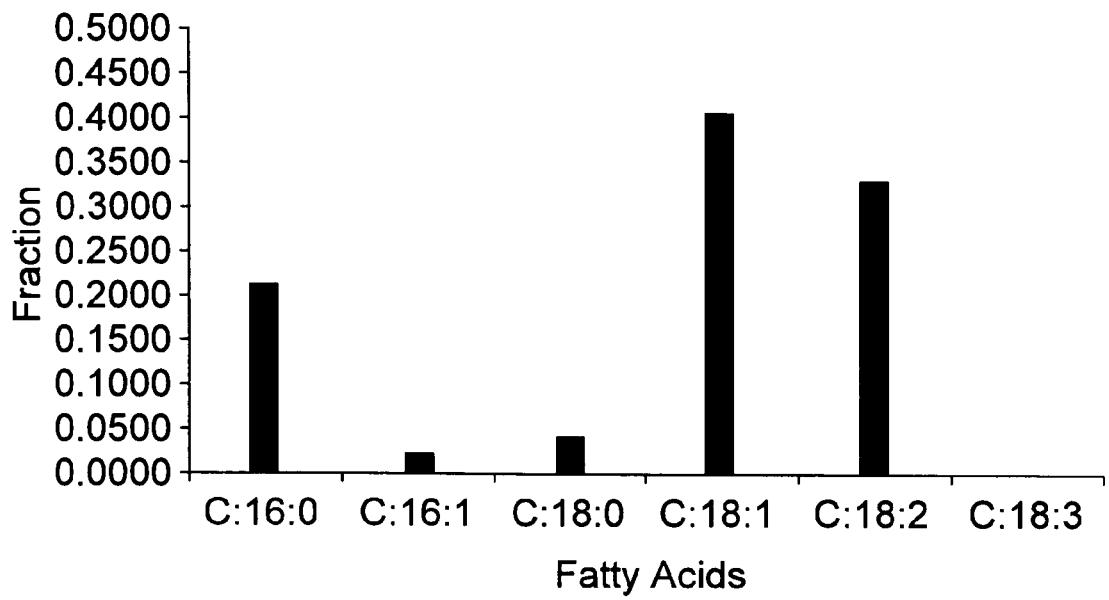
Fig. 2: Fatty Acid profile Peanut raised Moth
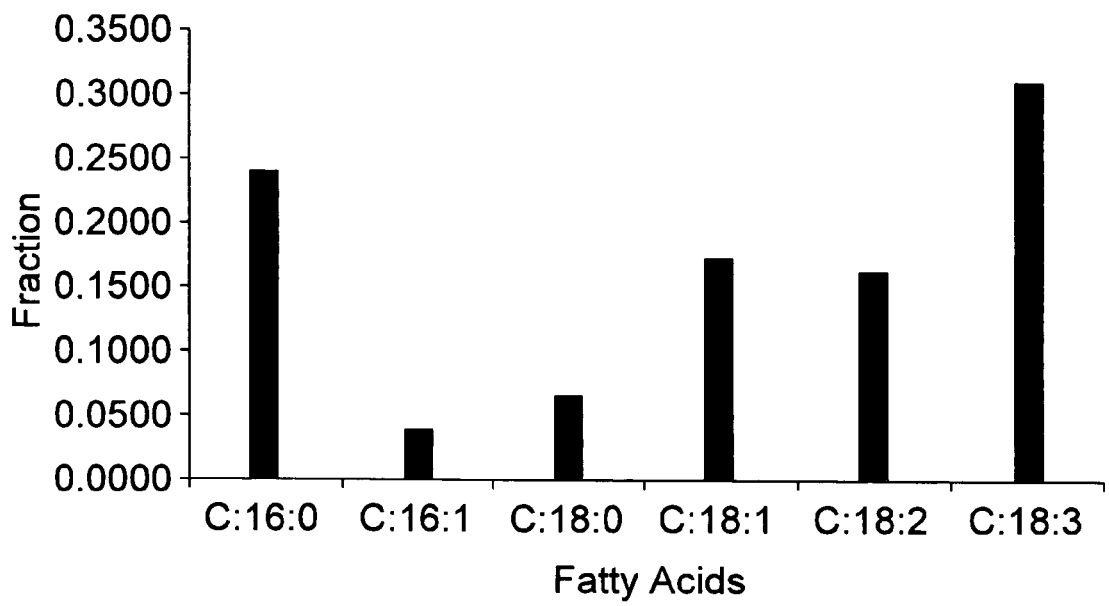
Fig. 3: Fatty Acid profile Tobacco raised Moth

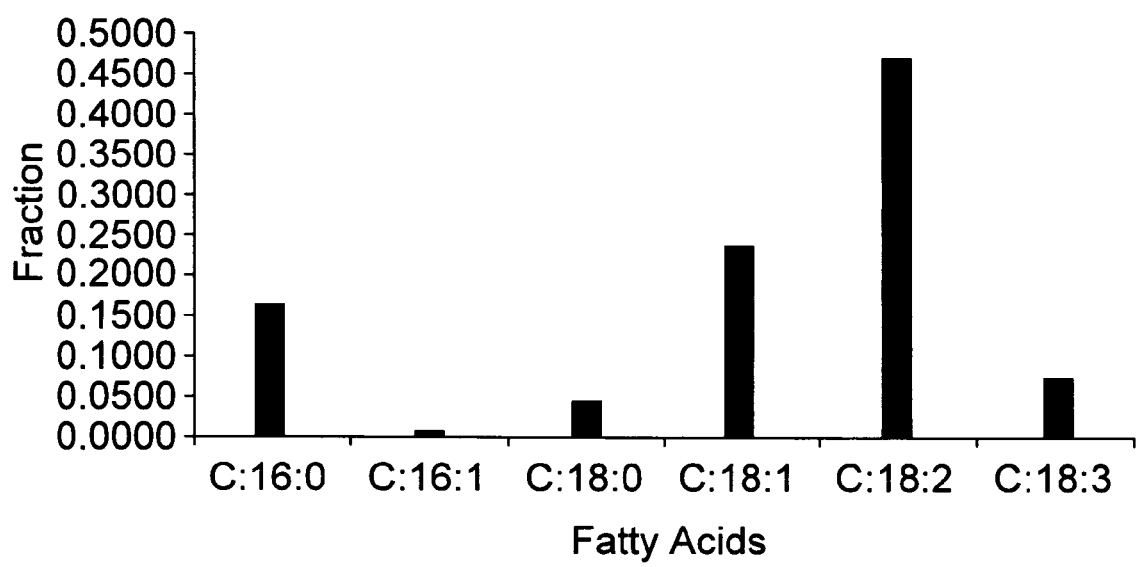
Fig. 4: Fatty Acid profile Soybean raised Moth

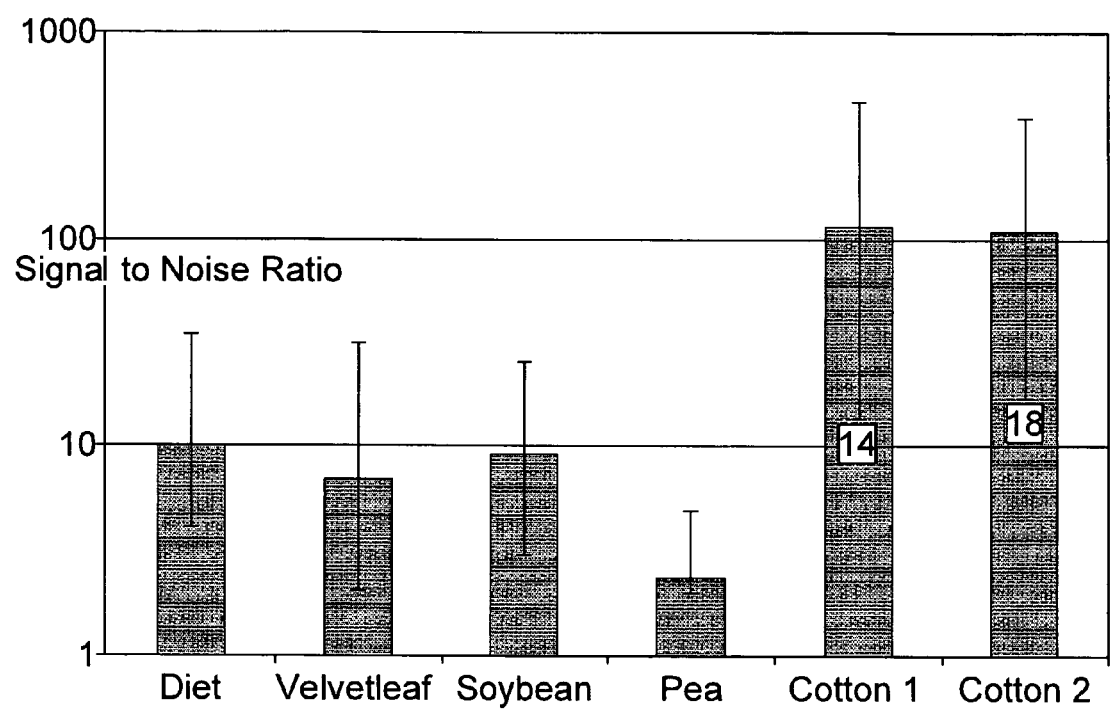
Fig. 5: Gossypol Results by Crop Source

METHODS FOR DETERMINING THE FEEDING HABITS OF AN ANIMAL

CROSS-REFERENCE TO RELATED APPLICATION

This application claims domestic priority from U.S. Provisional Application for Patent Ser. No. 60/732,593 filed Nov. 2, 2005, the disclosure of which is hereby incorporated by reference.

FIELD OF THE INVENTION

The present invention generally relates to methods for determining the feeding habits and feeding history of an animal, and more particularly, to methods for determining the host plants of pests.

BACKGROUND OF THE INVENTION

Pest-resistant transgenic crops are continually being developed to allow for increased crop yields while reducing the amount of pesticides required. However, the potential for pest resistance to the transgenic crops is widely recognized, and the agricultural community is anxious to establish protocols by which the emergence of completely unsusceptible pest populations can be significantly delayed or prevented.

One way to slow the rate at which pests evolve resistance to transgenic crops is to ensure the presence of a refuge where susceptible pests are not exposed to the pesticide. In theory, the adult pests which emerge from the refuge environment will disperse and breed with any pests which emerge from the recombinant fields, and if any of the insects which emerge from the recombinant fields have developed a level of resistance to the recombinant pesticidal proteins, the availability of that trait in the subsequent generations will be diluted, thereby reducing or delaying the onset of the emergence of a race which will be totally resistant to the recombinant plant.

Refuge areas may consist of portions of the crop of interest that are untreated (i.e., structured refuge) or other suitable crop and weedy hosts of the pest (i.e., alternative host refuge or natural refuge). Evaluating the refuge available for a pest that is capable of developing on multiple host plant species requires some means of evaluating the portion of the insect population that exists on the different potential hosts.

In today's regulatory environment, obtaining the approval of an appropriate regulatory agency for commercialization of a recombinant plant requires that a percentage of the entire crop that is planted containing a recombinant trait be planted as a refuge of non-recombinant or non-transgenic crops on a farm-by-farm basis. Refuge requirements increase farmers' labor and financial expenses, and are difficult to police. The added labor for planting and segregating the refuge and the likely lower yields within the refuge as a result of greater insect infestation are a disincentive for the farmer to comply with the regulatory requirements.

Thus, there remains a need for methods of determining the feeding habits and feeding history of animals, and particularly pests, such that more effective refuge areas can be determined or designed. Accordingly, it would be desirable to be able to screen or fingerprint an animal or population of animals in a manner that would readily identify patterns of movement and feeding habits or history.

SUMMARY OF THE INVENTION

There is now provided a method for determining whether an animal has ingested a plant of interest. The method comprises screening the animal for the presence of at least one indicator of a plant of interest.

There is also provided a high-throughput method for determining the feeding history of an animal. The method comprises collecting a tissue sample from a plurality of animals, placing the tissue samples into individual wells of a multi-well plate, and screening each tissue sample for the presence of one or more indicators of a plant of interest.

There is further provided a method for determining whether an animal has ingested one of several plants of interest. The method comprises collecting at least one tissue from the animal; determining the fatty acid profile of the tissue; and comparing the fatty acid profile of the tissue to a fatty acid profile of an animal known to have consumed the plant of interest during its lifecycle.

There is still further provided a method for determining whether the feeding stage of an insect has ingested a plant of interest. The method comprises screening the insect for the presence of at least one indicator selected from the group consisting of gossypol, nicotine, nornicotine, cotinine, norcotinine, resveratrol, genestein, daidzein, glycitein, derivatives thereof, and combinations thereof.

There is still further provided a method for determining whether a feeding stage of an insect has ingested a cotton plant. The method comprises determining the relative amounts of C16:1 and C18:1 in the fatty acid profile of the adult insect.

There is also provided a method for determining whether a feeding stage of an insect has ingested a peanut plant. The method comprises determining the relative amounts of C16:0, C18:1, and C18:2 in the fatty acid profile of the adult insect.

There is also provided a method for determining whether a feeding stage of an insect has ingested a tobacco plant. The method comprises determining the relative amounts of C16:0 and C18:3 in the fatty acid profile of the adult insect.

There is also provided a method for determining whether a feeding stage of an insect has ingested a soybean plant. The method comprises determining the relative amounts of C16:0, C18:1, C18:2, and C18:3 in the fatty acid profile of the adult insect.

There is still further provided a method for determining the natural refuge area for a pest relative to a transgenic crop. The method comprises trapping pests from the vicinity of a transgenic crop, screening the trapped pests for the presence of one or more indicators of at least one plant of interest, and determining the percentage of the pest population consuming a plant other than the transgenic crop.

Further features and benefits of the invention will be apparent to one skilled in the art from reading this specification.

BRIEF DESCRIPTION OF THE DRAWINGS

FIG. 1 is a bar graph depicting the fatty acid profiles of moths raised on cotton plants as determined in Example 1.

FIG. 2 is a bar graph depicting the fatty acid profile of moths raised on peanut plants as determined in Example 1.

FIG. 3 is a bar graph depicting the fatty acid profile of moths raised on tobacco plants as determined in Example 1.

FIG. 4 is a bar graph depicting the fatty acid profile of moths raised on soybean plants as determined in Example 1.

FIG. 5 is a graphical representation of signal to noise ratio determined in the gossypol validation study of Example 1.

DETAILED DESCRIPTION

There is now provided a method for determining whether an animal has ingested a plant of interest. The method comprises screening the animal for the presence of at least one indicator of a plant of interest.

Before further describing the invention, it is useful to understand the problem herein identified and addressed.

Animal behavior patterns have a variety of commercial implications in agriculture, land-use practices, conservation, real estate, etc. Patterns of movement are extrinsically tracked by radio transmitters, satellite technology, tagging, etc., but there are difficulties. For example, radio telemetry is not practical to use with smaller animals or animals that migrate long distances. Satellite technology is cost prohibitive. Tagging requires capture and recapture of a few animals in a group, and those animals may not be representative of the group.

Stable isotope methods have also been used to follow patterns of animal movement. Stable isotopes are naturally occurring stable forms of elements with differing nuclear masses. Stable isotopes are incorporated directly into animal tissues through the animal's diet. Although stable isotope methods do not rely on recapture of previously captured animals, additional assumptions must be made. For example, differences in diet, foraging location, and metabolism, differences in climate and altitude, and differences in bedrock composition and soil heterogeneity invariably affect the isotope patterns in animal tissue.

Gould et al. (2002) *Proc. Natl. Acad. Sci.* 99(26), 16581-16586 propose stable isotope assessment as a way to identify host plants utilized by *Helicoverpa zea* larvae (cotton bollworm), a crop pest. The stable carbon isotope (ratio of $^{13}C$ to $^{12}C$, commonly reported as $\delta^{13}C$) composition of $C_3$ plants such as cotton and soybeans is within a range of −20 to −32 0/00, and within a range of −9 to −17 0/00 for $C_4$ plants such as corn. Likewise, Bontemps et al. (2004) *Proc. R. Soc. Lond.* 271, 2179-2185 propose the use of $\delta^{13}C$ to distinguish between *Ostrinia nubilalis* (European corn borer) host plants. However, the use of $\delta^{13}C$ is restricted to comparison between $C_3$ plants and $C_4$ plants, and would not be useful, for example, for distinguishing moths reared as larvae on cotton and moths reared as larvae on soybeans.

In accordance with the present invention, Applicants have discovered a method for determining whether an animal has ingested a plant of interest which can be applied to a variety of plants. The method generally comprises screening the animal for the presence of at least one indicator of a plant of interest.

As used herein, an "indicator" of a plant of interest is any chemical compound which can be detected in or on an animal and which signifies that the animal or a feeding stage of the animal ingested the plant of interest. To be a successful indicator, the compound should be both specific to the plant and not metabolized or predictably metabolized by the animal upon ingestion. Preferably, the indicator is unique to the plant and causes a unique pattern change in the biochemical makeup of the animal. For example, in one embodiment the indicator is a biomarker. In another embodiment, the indicator is a chemical compound which is naturally found in the plant of interest, for example, nicotine or gossypol. In another embodiment, the indicator is the result of human manipulation of a plant of interest, for example, a genetic marker specific to a transgenic plant. In still other embodiments, the indicator is a chemical compound which is predictably metabolized by the animal after ingesting the plant of interest.

As used herein, the term "ingest" encompasses similar terms including, for example, consume, eat, drink, metabolize, digest, and absorb.

Screening an animal for the presence of an indicator may or may not require obtaining a sample from the animal. In embodiments requiring a sample, the sample may comprise tissue, hair, feather, saliva, sweat, tears, gut content, or excreta. In one embodiment, the method of the present invention comprises analyzing at least one tissue of the animal for the presence of an indicator of the plant. In a particular embodiment, at least one tissue of the animal includes the whole animal, for example, an insect. In other embodiments, illustrative tissues may include skin, hair, feathers, wings, internal organs, blood, plasma, lymph, or the like. A tissue can be an entire organ, for example, a liver. Alternatively, the tissue sample can be obtained by biopsy.

Generally, a tissue sample can be analyzed by any laboratory method or field test suitable for determining the presence of the indicator of interest. Illustrative methods of analysis include protein extraction, fatty acid extraction, immunoprecipitation, DNA extraction, RNA extraction, PCR, Northern blot analysis, Southern blot analysis, Western blot analysis, elemental composition, chromatography, mass spectroscopy, immunostaining, confocal microscopy, and fluorescent microscopy.

The methods of the present invention are generally useful in determining the feeding habits or feeding history of a wide variety of animals including humans and non-humans, vertebrates or invertebrates. In various embodiments the animal is an insect, a fish, a bird, a reptile, or a mammal. Further, the animal can be domesticated or wild.

In a particular embodiment, the methods of the present invention are used to determine the feeding history of an insect, for example, a pest insect. Contemplated insects generally include any insect identified as a pest to an economically important crop plant. Examples of pest insects include, without limitation, northern corn rootworm, western corn rootworm, southern corn rootworm, cotton bollworm, tobacco budworm, European corn borer, corn earworm, armyworm, plant bug, and stink bug.

Likewise, the plant of interest can include any plant consumed by an animal directly, or consumed indirectly through the food chain. In one embodiment, the plant of interest is an agricultural crop plant, for example, cotton, corn, canola, maize, tobacco, soybean, peanut, sunflower, rice, alfalfa, or wheat. In another embodiment, the plant of interest is a fruit plant or tree. In another embodiment, the plant of interest is a vegetable plant. In still another embodiment, the plant of interest is selected from the group consisting of sugar cane, cocoa plants and coffee plants.

As described above, suitable indicators include any chemical compound which can be detected in or on an animal and which signifies that the animal or a feeding stage of the animal ingested the plant of interest. In embodiments wherein the plant of interest is a crop plant, suitable indicators can be selected from the group consisting of a fatty acid, a tocopherol, a sugar, a flavonoid, nicotine, nornicotine, cotinine, norcotinine, gossypol, a plant protein, a mineral, a plant secondary metabolite, a derivative thereof, and a combination thereof.

Illustrative flavonoids include anthocyanins, flavanols, flavonones, flavonols, flavones, and isoflavones. Illustrative isoflavones include genestein, daidzein, and glycitein.

Illustrative tocopherols include RRR-tocopherol, beta-tocopherol, gamma-tocopherol, delta-tocopherol, tocotrienols, alpha-tocotrienol, and delta-trienol. Illustrative sugars include glucose, fructose, or maltose.

Illustrative fatty acids include C16:0, C16:1, C18:0, C18:1, C18:2, and C18:3.

Illustrative minerals include calcium, iron, magnesium, phosphorus, potassium, sodium, zinc, copper, and manganese.

Illustrative plant proteins include resveratrol.

Illustrative plant secondary metabolites include gossypol, and an alkaloid. Illustrative alkaloids include solanine.

In a particular embodiment when screening an animal for the ingestion of cotton, gossypol can be a suitable indicator. Gossypol is a polyphenolic aldehyde pigment present in the seeds, rootbark, and subepidermal glands of plants of the genus *Gossypium*, and in particular, cotton. Rojas et al. (1992) *Environmental Entomology* 21(3), 518-526 discuss gossypol distribution and metabolites in *Heliothis virescens* (tobacco budworm), a crop pest. The *Heliothis* larva feeds on crop plants including cotton. The authors report that the adult *Heliothis* moth contained 2.4% of the total gossypol ingested by the *Heliothis* larva.

Gossypol is uniquely related to the lysigenous glands of cotton (*Gossypium* spp.) and related plants. Work by Rojas, et al. demonstrated that the adult moth of *Heliothis virescens* contained 2.4% of the gossypol eaten by the larval stage. The study indicated all of the gossypol was as a bound form and no free gossypol was found. Thus analytical methods which can determine the presence of bound gossypol in the adult moth would allow moths that developed on cotton to be discriminated from those that developed on other hosts.

In another embodiment for determining whether an animal has ingested a tobacco plant, the animal may be screened for the presence of nicotine or a nicotine derivative. Generally, nicotine is a suitable indicator for the ingestion of tobacco plants. However, because nicotine is relatively abundant in the environment from sources other than tobacco, nicotine derivatives including metabolites of nicotine may be more preferred as an indicator for tobacco consumption. Examples of nicotine metabolites include cotinine, nomicotine, and norcotinine.

In a still further embodiment for determining whether an animal has ingested a soybean plant, the animal may be screened for the presence of one or more isoflavones. Suitable isoflavones include, for example, genisten, daidzein, or glycitein.

In another embodiment for determining whether an animal has ingested at least one plant of interest, the method comprises collecting at least one tissue from the animal; determining the fatty acid profile of the tissue; and comparing the fatty acid profile of the tissue to a fatty acid profile of an animal known to have consumed the plant of interest during its lifecycle. Generally, the fatty acid profile is determined by contacting the tissue sample with a solvent to extract fatty acids from the tissue sample. The extracted fatty acids are then transesterified to produce fatty acid methyl esters which can be further separated and detected to determine a fatty acid profile for the tissue sample.

In some embodiments, the presence of one fatty acid will determine whether an animal has ingested a plant of interest. In other embodiments, two or more fatty acids in combination will determine whether an animal has ingested a plant of interest. In still other embodiments, the fatty acid profile will determine whether an animal has ingested a plant of interest. The fatty acid profile can be any ratio of one or more fatty acids relative to the total fatty acids measured.

For example, it has been found that the relative amounts of $C16:1$ and $C18:1$ in the fatty acid profile of the animal can determine whether the animal consumed cotton plants. Further, the relative amounts of $C16:0$, $C18:1$, and $C18:2$ in the fatty acid profile of the animal is indicative of peanut plants; the relative amounts of $C16:0$, $C18:1$, $C18:2$, and $C18:3$ in the fatty acid profile of the animal is indicative of soybean plants; and the relative amounts of $C16:0$ and $C18:3$ in the fatty acid profile of the animal is indicative of tobacco plants.

In some embodiments, the method comprises first analyzing a tissue of the animal for the presence of an indicator of a plant of interest, and second determining the fatty acid profile of the tissue and comparing the fatty acid profile of the tissue to a fatty acid profile indicative of feeding on the plant. In other embodiments, the method comprises first determining the fatty acid profile of the tissue and comparing the fatty acid profile of the tissue to a fatty acid profile of an animal known to have consumed the plant, and second analyzing the tissue for the presence of an indicator of the plant.

In a particular embodiment, the methods of the present invention are configured to provide for a high-throughput method for determining the feeding characteristics of an animal. The method generally comprises collecting tissue samples from a plurality of animals and placing the samples into individual wells of a multi-well plate. Each sample in the multi-well plate is then screened for the presence of at least one indicator of a plant of interest or to determine the fatty acid profile of the tissue samples as described above.

The methods and concepts described herein for tracking the feeding habits or feeding history of an animal have multiple applications. In a particular embodiment, the screening methods described herein can be used to determine the natural refuge areas of pests relative to a transgenic crop. Such a method comprises trapping pests from the vicinity of a transgenic crop; screening the trapped pests for the presence of one or more indicators of at least one plant of interest; and determining the percentage of the pest population consuming a plant other than the transgenic crop. Alternatively or additionally, the method may comprise collecting at least one tissue from the trapped pests; determining the fatty acid profile of the tissue; and comparing the fatty acid profile of the tissue to a fatty acid profile of a pest known to have consumed the plant of interest during its lifecycle before determining the percentage of the pest population consuming a plant other than the transgenic crop. Accordingly, product developers, scientists and regulatory authorities involved in determining refuge areas for pests can use the information relating to the feeding habits and feeding history of the pests to determine whether the natural refuge area for those pests is sufficient to partly or completely replace the need for farmers to plant structured refuges for the transgenic crop of interest on their farms, thereby significantly delaying or preventing the development of resistant pest populations while maximizing crop yield.

EXAMPLE

The following example is merely illustrative in nature and should not be interpreted in a limiting sense.

This example demonstrates a method of the invention for determining whether an animal has ingested a plant of interest. The experiment comprised feeding larval stage tobacco budworm moths one of tobacco, cotton, soybean, or peanut plants. After metamorphosis, the adult moths were analyzed for their fatty acid profile. The profiles were used to determine differences in the lipid fatty acid profiles for each of the host plant species. The moths were then analyzed for the presence of cotinine (a nicotine metabolite) to determine whether the moths developed on tobacco. Finally, the moths were analyzed for gossypol to determine whether the moths developed on cotton.

Although the analyses in this experiment were completed in sequence, it is important to note that the analyses can be carried out in any order or independently of each other.

Extraction of Fatty Acids

Adult moths were collected, freeze-dried, weighed, and individually placed into 2 mL wells of a 96-well plate. The moths were then ground by adding a glass bead to each well, capping the plate and placing the plate on a grinder as described, for example, in U.S. Pat. No. 6,880,771, which is incorporated herein by reference. During grinding, the grinder shook the plate at 800 rpm for 60 seconds. After grinding, diethyl ether (1 mL) was added to each well. The plate was again capped, and vortexed for 15 minutes to extract fatty acids from the moth matrix into the diethyl ether. The fatty acids in the diethyl ether were then placed into a 2 mL well in a new 96-well plate for transesterification. The original 96-well plate containing the moths was placed under a dry stream of nitrogen to remove residual ether, and then capped and stored at −20° C. for later cotinine and gossypol determinations.

Transmethylation of Extracted Fatty Acids

Methyl acetate (20 μL) and sodium methoxide (40 μL) were added to each well containing the fatty acids in diethyl ether. The plate was again vortexed for 30 seconds and the solution was allowed to stand at room temperature for 10-40 minutes. Next, diethyl ether saturated with oxalic acid (30 μL) was added and the plate vortexed for at least 20 seconds. The ether solution was then removed using a dry stream of nitrogen. After drying, hexane (1.5 mL) was added to each well and the plate vortexed. A sample (1 mL) from each well was transferred to an autosampler vial for analysis by gas chromatography.

Gas Chromatography and Mass Spectrometry Conditions

The gas chromatograph comprised a DB-FFAP column, 15 meters long, 0.25 mm in diameter, and a film thickness of 0.25 microns. The inlet temperature was 250° C. and the injection was set for a split injection (ratio of 6:1). Each sample (1 μL) was injected with helium as the carrier gas at a flow rate of 0.8 mL/minute. The column was operated at a temperature of 85° C. for 30 seconds, then ramped to 150° C. at a rate of 25° C./minute, then ramped to 250° C. at a rate of 17° C./minute. The column was then maintained at 250° C. for 3 minutes.

The detector was an electron impact mass sensitive detector, with the mass detection set between 60 and 350 m/z. The fatty acid integrated areas were obtained for C16:0, C16:1, C18:0, C18:1, C18:2, and C18:3.

Cotinine Analysis

The ground moths remaining in the 96 well plate wells were analyzed for the presence of cotinine according to the following:

Extraction of Cotinine

An extraction solution was prepared by adding acetic acid (50 mL) to a 1000 mL volumetric flask followed by the addition of methanol (200 mL). Deionized water was added to the flask to bring the total volume to 1000 mL. 40% NaOH was added to the extraction solution to increase the pH above 11.

Extraction solution (1 mL) was added to each well containing a ground moth. Next, deuterated cotinine (20 μL) was added as an internal standard. The plate was then capped by placing parafilm over the top of the plate then pressing the lid onto the plate over the parafilm. The capped plate was first vortexed for 15 minutes, then centrifuged. The liquid layer from each well was removed and added to 8 mL vials. A second volume of extraction solution (1 mL) was added to each well, the plate vortexed for 5 minutes, and then centrifuged. The liquid layer from each well was added to the previous extract in the respective 8 mL vial. To each 8 mL vial, 40% NaOH (150 μL) was added, followed by deionized water (4 mL). The 96-well plate containing the moth residue was dried under a dry stream of nitrogen and stored at −20° C. until further analysis.

A divinyl benzene 100 mg solid phase extraction (DVB SPE) was used to remove the cotinine from the extraction solution. The DVB SPE was prepared by washing the column with ethanol (2 mL), followed by deionized water (2 mL). Then, the cotinine in extraction solution was passed through the column followed by additional deionized water (1 mL). The column was dried for 5-30 minutes by passing air through the column. Subsequently, the column was washed with 20% methanol in ether (3 mL) to elute the cotinine from the column. The methanol/ether was removed from the cotinine using a dry stream of nitrogen. The cotinine was resuspended in methanol/ether (150 μL), and the sides of the column were washed down to avoid losing any sample. The samples were placed into autosampler vials for GC/MS analysis.

Gas Chromatography and Mass Spectrometry

The gas chromatograph comprised a DB-5 column, 15 meters long, 0.25 mm inner diameter, and a film thickness of 0.25 μm. The inlet temperature was 285° C. and the injection was set for a split/splitless injection (ratio of 6:1). One microliter of each sample was injected with helium as the carrier gas and a flow rate of 2.1 mL/minute. The column temperature started at 100° C., held at that temperature for 0.1 minutes, then ramped to 175° C. at a rate of 40° C./minute, followed by a 30° C./minute ramp to 300° C.

The mass spectrometer used was a Leco Pegasus III time of flight, with electron impact ionization energy of 70 eV and a 50 second solvent delay. The scan range was from 50-210 m/z with 15 scans per second. The ion source temperature was 200° C.

Quantification of cotinine in the samples was determined by measuring the ratio of the area of m/z 176 to the area of m/z 180, where m/z 180 was the deuterated cotinine standard. The cotinine standard in each sample was used to determine retention time. Cotinine data were measured in parts per billion, with a detection limit of around 1 part per billion.

Gossypol Analysis

The remains of the ground moths in the 96-well plate were analyzed for the presence of gossypol according to the following:

Extraction of Gossypol

Most gossypol found in moths has been metabolized and bound to protein. To extract gossypol in the bound form, the complex can be derivatized by creating a Shiff's base with aniline forming dianilino-gossypol. The dianilino-gossypol can then be isolated from the moth matrix using DVB SPE. Both steps are described in detail below.

Derivatizing agent was prepared by mixing aniline (1 mL), glacial acetic acid (5 mL), and dimethylformamide (44 mL). The derivatizing agent can be stored at 4° C. for one week. Deuterated derivatizing agent was prepared by mixing deuterated aniline (0.1 mL d5-aniline), acetic acid (0.5 mL), and dimethylformamide (4.4 mL). The deuterated derivatizing agent can be stored at 4° C. for one week.

Derivatizing agent (1 mL) was added to each well containing a ground moth. The plate was covered with parafilm and a cap pressed over the parafilm to seal each well. The plate was vortexed for 1 minute, then the cap and seal removed and the plate covered with foil. The plate was heated at 80-90° C. for 1 hour in an oven or heated well plate holder. After removing from the heating system and cooling, the plate was again covered with parafilm and capped to seal each well. The plate was centrifuged for 5 minutes at 2500-3000 rpm.

A DVB SPE was used to remove the gossypol from the derivatizing agent. A DVB SPE 96 well plate was prepared by washing the columns with acetone (0.5 mL), followed by methanol (0.5 mL). The columns were then left wet with a solution comprising an equal mixture of water and DMF (0.5 mL).

To avoid cross contamination, the cap and parafilm were carefully removed from the 96 well plate containing moths and derivatizing agent. Next, water (0.5 mL) was added to each well. Each sample was transferred to respective wells in the DVB SPE 96 well plate and allowed to pass through the column. Additional DMF (0.5 mL) was added to the original 96 well plate containing the moth residue, the plate was covered with parafilm and then capped, vortexed for 1 minute, and centrifuged for 5 minutes at 3000 rpm. After centrifuging, water (0.5 mL) was added to each well and the samples transferred to respective wells in the DVB SPE 96 well plate.

After the samples passed through the columns, the columns were rinsed with 20:80 water to methanol (0.5 mL) and followed by 5:95 acetone to methanol (0.5 mL). Subsequently, the gossypol was eluted from the column with acetone (500 μL) into a 2 mL or 1.5 mL 96 well plate. The acetone was removed from the samples and the samples were dried with a gentle stream of nitrogen. The samples were stored at −20° C. until analysis by electrospray ionization/mass spectrometry/mass spectrometry (ESI/MS/MS).

HPLC/ESI/MS/MS Determination of Gossypol

To each sample, acetone (200 μL) was added and the samples were mixed. Next, a solution comprising 5 μg/mL deuterated derivatized dianilino-gossypol (20 μL) was added to each sample as an internal standard. The samples were capped and vortexed, then transferred to a 0.5 mL 96 well plate for analysis.

The HPLC used a short column (Zorbax Eclipse XBD-C18 commercially available from Agilent Technologies, Inc.) with a dual solvent mobile phase. Solvent A was 10% water in methanol and solvent B was 2:1 acetonitrile to acetone. The flow rate was 0.25 mL/minute with a gradient as shown in Table 1.

TABLE 1

HPLC solvent gradient

| Time (minutes) | % B with respect to A |
|---|---|
| 0 | 0 |
| 2 | 0 |
| 2.1 | 5 |
| 2.5 | 50 |
| 4 | 60 |
| 4.1 | 0 |
| 5 | 0 |

The mass spectrometer was a Micromass Quattro Ultima LC/MS/MS detector by Waters, and contained a triple quadrupole mass spectrometer with negative electrospray ionization. Because the HPLC did not provide the correct ionization matrix for negative electrospray ionization of the dianilino-gossypol, 0.6% $NH_4OH$ in methanol was introduced past the HPLC column at a flow rate of 0.05 mL/minute. Post-column mixing of the NH4OH in MeOH with the HPLC eluant was achieved using a mixing T-connection. In MS/MS mode, the first quadrupole was used to select 667.3 as the mass to charge ratio that represented the negative ion of dianilino-gossypol. In the second quadrupole, the 667.3 mass to charge ratio was fragmented in a collision cell. The third quadrupole was used to select the fragment ion, monoanilino-gossypol, which had a mass to charge ratio of 574.2 as a result of the loss of an aniline. Detection of the second fragment ion provides improved specificity and increased signal to noise ratios.

Semi-quantization of gossypol was determined by the ratio of the peak area of the 574.2 m/z to the peak area of the internal standard, deuterated dianilino-gossypol. These ratios were then compared to standards, blanks, and results from laboratory reared control moths to determine whether gossypol was present.

Results

As described above, Tobacco budworm moths raised as larvae on tobacco, cotton, soybean, and peanut plants were analyzed for their fatty acid profile, the presence of cotinine, and the presence of gossypol.

To build the fatty acid profile of each plant host, a total ion chromatogram was integrated and the area for each fatty acid (C16:0, C16:1, C18:0, C18:2, and C18:3) was obtained and added together for a total. The fraction of one fatty acid out of the total is shown below in Tables 2 through 5. The comparisons of all four host plants show that each has a unique fatty acid profile which can be used to distinguish it from the others.

TABLE 2

Fatty acid ratios for moths raised on peanut plants

| Fatty acid | Moth 1 | Moth 2 | Moth 3 | Moth 4 | Moth 5 | Average |
|---|---|---|---|---|---|---|
| C16:0 | 0.2096 | 0.1690 | 0.1866 | 0.1816 | 0.2087 | 0.1911 |
| C16:1 | 0.0082 | 0.0044 | 0.0065 | 0.0083 | 0.0228 | 0.0100 |
| C18:0 | 0.0321 | 0.0291 | 0.0261 | 0.0215 | 0.0421 | 0.0302 |
| C18:1 | 0.5010 | 0.5414 | 0.5109 | 0.5569 | 0.3996 | 0.5020 |
| C18:2 | 0.2467 | 0.2561 | 0.2676 | 0.2317 | 0.3267 | 0.2658 |
| C18:3 | 0.0024 | 0.0000 | 0.0023 | 0.0000 | 0.0000 | 0.0009 |

TABLE 3

Fatty acid ratios for moths raised on cotton plants

| Fatty acid | Moth 1 | Moth 2 | Moth 3 | Moth 4 | Average |
|---|---|---|---|---|---|
| C16:0 | 0.2959 | 0.3441 | 0.2667 | 0.2848 | 0.2979 |
| C16:1 | 0.0549 | 0.0581 | 0.0366 | 0.0313 | 0.0452 |
| C18:0 | 0.0212 | 0.0085 | 0.0169 | 0.0396 | 0.0216 |
| C18:1 | 0.4276 | 0.4989 | 0.5179 | 0.4142 | 0.4647 |
| C18:2 | 0.1243 | 0.0594 | 0.1122 | 0.1497 | 0.1114 |
| C18:3 | 0.0761 | 0.0310 | 0.0497 | 0.0805 | 0.0593 |

TABLE 4

Fatty acid ratios for moths raised on soybean plants

| Fatty acid | Moth 1 | Moth 2 | Moth 3 | Moth 4 | Moth 5 | Average |
|---|---|---|---|---|---|---|
| C16:0 | 0.1141 | 0.1677 | 0.1917 | 0.1694 | 0.1677 | 0.1621 |
| C16:1 | 0.0054 | 0.0117 | 0.0100 | 0.0033 | 0.0113 | 0.0084 |
| C18:0 | 0.1012 | 0.0254 | 0.0231 | 0.0373 | 0.0257 | 0.0426 |
| C18:1 | 0.1686 | 0.2538 | 0.2814 | 0.2447 | 0.2557 | 0.2408 |
| C18:2 | 0.4698 | 0.4783 | 0.4324 | 0.4869 | 0.4772 | 0.4689 |
| C18:3 | 0.1408 | 0.0631 | 0.0614 | 0.0583 | 0.0623 | 0.0772 |

TABLE 5

Fatty acid ratios for moths raised on tobacco plants

| Fatty acid | Moth 1 | Moth 2 | Moth 3 | Moth 4 | Moth 5 | Average |
|---|---|---|---|---|---|---|
| C16:0 | 0.3133 | 0.1612 | 0.2797 | 0.2939 | 0.1520 | 0.2400 |
| C16:1 | 0.0756 | 0.0599 | 0.0150 | 0.0281 | 0.0200 | 0.0397 |
| C18:0 | 0.0235 | 0.0776 | 0.0510 | 0.0534 | 0.1303 | 0.0671 |
| C18:1 | 0.2122 | 0.1991 | 0.1391 | 0.1380 | 0.1773 | 0.1731 |
| C18:2 | 0.1746 | 0.2544 | 0.1314 | 0.1222 | 0.1446 | 0.1654 |
| C18:3 | 0.2008 | 0.2478 | 0.3839 | 0.3644 | 0.3758 | 0.3145 |

Soft Independent Modeling for Class Analogy (SIMCA) was used to develop a supervised classification model based upon the fatty acid profiles of the moths raised on each of the four crop plants. SIMCA model development generated a separate Principal Component Analysis (PCA) model for each of the four crop plants, or a class model. A new, unknown sample was classified with each PCA model and its class membership determined by the minimum distance of the unknown sample from the PCA class model. See FIGS. 1 to 4. The $S_i S_o$ versus $H_o$ plot shows the sample-to-model distance relative to the average model distance ($S_i/S_o$) on the abscissa and the leverage for each sample on the ordinate axis. The class limits are shown as horizontal and vertical lines at the 5% significance level. Unknown samples near the origin within both lines can be classified as members of the class model. Samples outside these lines can be classified as not belonging to the class model. FIGS. 1 to 4 show that the fatty acid profile data can be used to classify moth samples according to the host plant that the larvae fed on before metamorphosis. Table 6 shows the distance between models. The larger the inter-model distance, the greater the difference that exists between classes. Typically, a model difference greater than 3 indicates class models that are significantly different. With values in the range of 200-45,000, the class models are significantly different and can be used to classify new samples according to their class.

TABLE 6

Model distance between cotton, tobacco, soy, and peanut plants

|  | Cotton PCA | Tobacco PCA | Soy PCA | Peanut PCA |
|---|---|---|---|---|
| Cotton PCA | 1 | 317 | 244 | 1735 |
| Tobacco PCA | 317 | 1 | 253 | 45430 |
| Soy PCA | 244 | 253 | 1 | 1744 |
| Peanut PCA | 1735 | 45430 | 1744 | 1 |

Validation assays for gossypol were run as two separate sets on two different days. The majority of insects were raised on cotton. On the first set on day one, insects fed on velvetleaf, soybean and pea were included for comparison. This set would be expected to prove negative for gossypol. On the second day, insects fed on artificial diet were included as negative controls. On both days, blanks and standards also were run as additional assay controls.

Results in FIG. 5 are expressed as the signal to noise ratio recorded by the electrospray/mass spectrometer which has given the most consistent results. Other response parameters from the mass spectrometer, such as peak area, also can be used. The minimum, average and maximum signal to noise ratio is shown for each of the treatment groups: insects reared on artificial diet, velvetleaf, soybean, pea or cotton (with the cotton-fed insects from the two days presented separately). A cut-off value of 12 for the signal to noise ratio was chosen as the value to determine if gossypol was present or not (if greater, then the sample was positive; if less than or equal to, it was negative). Using these criteria, the cotton-fed insects were always identifiable as positive for gossypol in the assay. For cotton raised moths the signal to noise ratio typically was greater than 100, almost always greater than 30, and never less than 14. The minimum values on the two days were 14 and 18 respectively, with a total of more than 50 cotton-fed insects assayed on each of the days. The signal to noise criteria depend on the overall method and thus could vary from laboratory to laboratory. It is therefore important that a validation study be-performed to set the criteria in a way that minimizes false negatives.

Using the signal to noise criteria, the results of the validation study for the gossypol HPLC-MS assay are shown in Table 7. All cotton fed moths were found to be positive for gossypol. The moths raised on other non gossypol containing plants had a false positive rate. Table 7 also shows that for the moths raised on non-gossypol plants there was a false positive rate. That is the moths would have been identified as having been raised on cotton when they had not been. For example, 4 of the 28 velvetleaf fed moths tested were identified as having fed on cotton.

With a signal to noise set for detection of gossypol at 12:1, the assay allows for the successful identification of all insects from cotton (gossypol positive) but will have a false positive rate of about 15%. That is, some number of insects that did not feed on cotton conservatively will be identified as from cotton.

TABLE 7

Results of validation study

|  | Diet | Velvetleaf | Soybean | Pea | Cotton 1 | Cotton 2 |
|---|---|---|---|---|---|---|
| Negative | 27 | 24 | 5 | 5 | 0 | 0 |
| Positive | 6 | 4 | 2 | 0 | 56 | 58 |

What is claimed is:

1. A method for determining whether the feeding stage of an animal has ingested a plant of interest, the method comprising:
   screening the animal to determine a fatty acid profile of the animal, wherein screening the animal includes:
   collecting a tissue sample from the animal;
   extracting fatty acids from the tissue sample; and
   analyzing the extracted fatty acids to determine the fatty acid profile of the animal;
   comparing the fatty acid profile of the screened animal to a fatty acid profile of an animal known to have consumed a plant of interest during its lifecycle to determine whether the screened animal has ingested the plant of interest.

2. The method of claim 1, further comprising screening the animal for the presence of at least one indicator, wherein the at least one indicator is selected from the group consisting of nicotine, nornicotine, cotinine, norcotinine, and gossypol.

3. The method of claim 1, wherein the animal is a pest.

4. The method of claim 1, wherein the animal is an insect.

5. The method of claim 1, wherein the plant of interest is a crop plant.

6. The method of claim 1, wherein the plant of interest is a crop plant selected from the group consisting of cotton, corn, canola, maize, tobacco, soybean, peanut, sunflower, rice, alfalfa, and wheat.

7. The method of claim 1, wherein the animal is a cotton bollworm moth or a tobacco budworm moth.

8. The method of claim 1, wherein screening the animal further includes:
- transesterifying the extracted fatty acids to produce a mixture of fatty acid methyl esters; and
- separating and detecting the mixture of fatty acid methyl esters to determine the fatty acid profile of the animal.

9. The method of claim 1, wherein the method is conducted in a high-throughput format.

10. The method of claim 9, further comprising screening the animal for the presence of at least one indicator, wherein the at least one indicator is selected from the group consisting of a tocopherol, a sugar, a flavonoid, an alkaloid, a plant protein, a genetic marker, a mineral, a derivative thereof, and a combination thereof.

11. The method of claim 9, further comprising screening the animal for the presence of at least one indicator, wherein the at least one indicator is selected from the group consisting of nicotine, nornicotine, cotinine, norcotinine, and gossypol.

12. The method of claim 1, wherein the animal is an insect and the plant of interest is a cotton plant, and wherein screening the animal further includes determining the relative amounts of C16:1 and C18:1 in the fatty acid profile of the insect for use in determining whether the insect has ingested a cotton plant.

13. The method of claim 12, further comprising screening the insect for the presence of gossypol.

14. The method of claim 1, wherein the animal is an insect and the plant of interest is a peanut plant, and wherein screening the animal further includes determining the relative amounts of C16:0, C18:1, and C18:2 in the fatty acid profile of the insect for use in determining whether the insect has ingested a peanut plant.

15. The method of claim 14, further comprising screening the insect for the presence of resveratrol.

16. The method of claim 1, wherein the animal is an insect and the plant of interest is a tobacco plant, and wherein screening the animal further includes determining the relative amounts of C16:0 and C18:3 in the fatty acid profile of the insect for use in determining whether the insect has ingested a tobacco plant.

17. The method of claim 16, further comprising screening the insect for the presence of nicotine and/or a nicotine derivative.

18. The method of claim 1, wherein the animal is an insect and the plant of interest is a soybean plant, and wherein screening the animal further includes determining the relative amounts of C16:0, C18:1, C18:2, and C18:3 in the fatty acid profile of the insect for use in determining whether the insect has ingested a soybean plant.

19. The method of claim 18, further comprising screening the insect for the presence of at least one isoflavone.

20. A method for determining the natural refuge area for pests relative to a transgenic crop, the method comprising:
- trapping pests from the vicinity of a transgenic $C_3$ crop and/or trapping pests from the vicinity of a transgenic $C_4$ crop;
- screening the trapped pests for the presence of one or more indicators of at least one plant of interest, wherein the at least one plant of interest includes a $C_3$ plant other than the transgenic $C_3$ crop and/or a $C_4$ plant other than the transgenic $C_4$ crop; and
- determining a percentage of the pests consuming the $C_3$ plant other than the transgenic $C_3$ crop and/or determining a percentage of the pests consuming the $C_4$ plant other than the transgenic $C_4$ crop;
- wherein the percentage of the pests consuming the $C_3$ plant other than the transgenic $C_3$ crop and/or the percentage of the pests consuming the $C_4$ plant other than the transgenic $C_4$ crop indicates the natural refuge area.

21. The method of claim 20, wherein the one or more indicators are selected from the group consisting of a fatty acid, a tocopherol, a sugar, a flavonoid, an alkaloid, a plant protein, a genetic marker, a mineral, a derivative thereof, and a combination thereof.

22. The method of claim 21, wherein the one or more indicators are selected from the group consisting of nicotine, nornicotine, cotinine, norcotinine, and gossypol.

23. The method of claim 20, wherein the one or more indicators include a fatty acid, and wherein screening the trapped pests includes collecting at least one tissue from the trapped pests, and determining a fatty acid profile of the at least one tissue; the method further comprising:
- comparing the fatty acid profile of the at least one tissue to a fatty acid profile of a pest known to have consumed a plant of interest during its lifecycle to determine whether the trapped pests have ingested the plant of interest.

24. The method of claim 20, wherein the pests are insects.

* * * * *